(12) United States Patent
Morishima et al.

(10) Patent No.: US 10,413,699 B2
(45) Date of Patent: Sep. 17, 2019

(54) SLEEP GUIDANCE DEVICE AND CONTROL METHOD

(71) Applicant: YAMAHA CORPORATION, Hamamatsu-shi (JP)

(72) Inventors: Morito Morishima, Fukuroi (JP); Kiyoshi Yamaki, Iwata (JP); Takehiko Kawahara, Hamamatsu (JP); Atsushi Ishihara, Iwata (JP)

(73) Assignee: YAMAHA CORPORATION, Hamamatsu-Shi (JP)

( * ) Notice: Subject to any disclaimer, the term of this patent is extended or adjusted under 35 U.S.C. 154(b) by 249 days.

(21) Appl. No.: 15/655,954

(22) Filed: Jul. 21, 2017

(65) Prior Publication Data

US 2017/0319817 A1    Nov. 9, 2017

Related U.S. Application Data

(63) Continuation of application No. PCT/JP2016/052177, filed on Jan. 26, 2016.

(30) Foreign Application Priority Data

Jan. 30, 2015   (JP) .................................. 2015-016225

(51) Int. Cl.
*A61M 21/00*   (2006.01)
*A61M 21/02*   (2006.01)
(Continued)

(52) U.S. Cl.
CPC ............ *A61M 21/02* (2013.01); *A61B 5/0205* (2013.01); *A61B 5/02108* (2013.01); *A61B 5/0476* (2013.01); *A61B 5/113* (2013.01); *A61B 5/1116* (2013.01); *A61B 5/486* (2013.01); *A61B 5/4812* (2013.01); *A61B 5/6814* (2013.01); *A61B 5/6824* (2013.01); *A61B 5/6887* (2013.01); *A61B 5/6891* (2013.01); *A61B 5/7405* (2013.01); *A61B 5/0022* (2013.01); *A61B 5/7278* (2013.01); *A61M 2021/0016* (2013.01); *A61M 2021/0022* (2013.01); *A61M 2021/0027* (2013.01); *A61M 2021/0044* (2013.01);
(Continued)

(58) Field of Classification Search
CPC ............................ A61M 21/02; A61B 5/0205
USPC ..................................................... 600/26–28
See application file for complete search history.

(56) References Cited

FOREIGN PATENT DOCUMENTS

JP   H04269972 A   9/1992
JP   2004344284 A  12/2004
(Continued)

OTHER PUBLICATIONS

International Search Report issued in Intl. Appln. No. PCT/JP2016/052177 dated Apr. 5, 2016. English translation provided.
(Continued)

*Primary Examiner* — John P Lacyk
(74) *Attorney, Agent, or Firm* — Rossi, Kimms & McDowell LLP (57) ABSTRACT

Provided is a sleep guidance device that serves to control a stimulus imparter for imparting stimuli to a human subject. The sleep guidance device acquires a biorhythm of the human subject; estimates sleep depths of the human subject from the acquired biorhythm of the human subject; and controls the stimulus imparter to impart a stimulus to the human subject in accordance with the acquired biorhythm of the human subject, and from among the sleep depths, a current sleep depth estimated for the human subject.

8 Claims, 8 Drawing Sheets

(51) Int. Cl.
  *A61B 5/00*    (2006.01)
  *A61B 5/0205*  (2006.01)
  *A61B 5/021*   (2006.01)
  *A61B 5/0476*  (2006.01)
  *A61B 5/11*    (2006.01)
  *A61B 5/113*   (2006.01)

(52) U.S. Cl.
  CPC . *A61M 2205/3303* (2013.01); *A61M 2230/04* (2013.01); *A61M 2230/10* (2013.01); *A61M 2230/63* (2013.01)

(56) References Cited

FOREIGN PATENT DOCUMENTS

| | | |
|---|---|---|
| JP | 2006043304 A | 2/2006 |
| JP | 2015013046 A | 1/2015 |

OTHER PUBLICATIONS

Written Opinion issued in Intl. Appln. No. PCT/JP2016/052177 dated Apr. 5, 2016.

SLEEP GUIDANCE DEVICE AND CONTROL METHOD

TECHNICAL FIELD

The present invention relates to a sleep guidance device used to improve sleep quality and the like.

BACKGROUND ART

Recently, there have been proposed technologies for improving sleep of a human subject by detecting biorhythms of the human subject, such as body motion, respiration and heartbeat, and generating a sound in accordance with the detected biorhythms (for example, see Japanese Patent Application Laid-Open Publication No. H4-269972). In addition, there have also been proposed technologies for adjusting, in accordance with a relaxation state of a human subject, at least one of a type, a loudness, and a tempo of a sound generated (for example, see Japanese Patent Application Laid-Open Publication No. 2004-344284).

During sleep, rapid eye movement (REM) sleep, which is characterized by light sleep, and non-REM sleep, which is characterized by deep sleep, alternate in cycles of approximately 90 minutes. However, differences in cycles of REM sleep and non-REM sleep exist between individuals. Moreover, a surrounding environment, a period between sleep onset and awakening, as well as time changes in sleep depths may not always be the same for a single human subject.

SUMMARY OF THE INVENTION

The present invention has been made in consideration of the aforementioned circumstances, and has as an object to provide a sleep guidance device that improves sleep quality and sleep satisfaction.

To achieve the above-stated object, a sleep guidance device according to one aspect of the present invention serves to control a stimulus imparter for imparting a stimulus to a human subject, the device having: an acquirer configured to acquire a biorhythm of the human subject; the stimulus imparter configured to impart a stimulus to the human subject; a sleep depth estimator configured to estimate sleep depths of the human subject from the biorhythm of the human subject acquired by the acquirer; and a stimulus controller configured to control the stimulus imparter to impart a stimulus to the human subject in accordance with the biorhythm of the human subject acquired by the acquirer, and from among the sleep depths, a current sleep depth estimated by the sleep depth estimator for the human subject.

MODES FOR CARRYING OUT THE INVENTION

Embodiments of the present invention will be explained below with reference to drawings.

Figure 1:
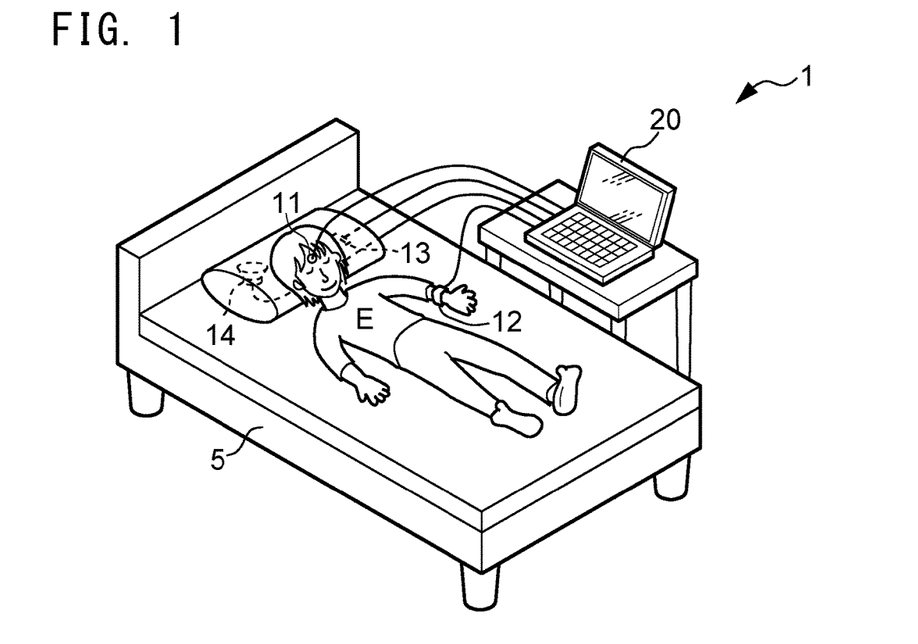
FIG. 1 illustrates an overall configuration of a system including a sleep guidance device according to an embodiment.

FIG. 1 illustrates an overall configuration of a system 1 including a sleep guidance device 20 according to an embodiment. As illustrated in the drawing, the system 1 includes sensors 11, 12 and 13, a loudspeaker 14, and the sleep guidance device 20. The system 1 aims to improve sleep quality, etc., and in turn lead to better sleep satisfaction by causing a sound that is output from the loudspeaker 14 to be heard or perceived by a human subject E lying on his/her back on a bed 5.

The forehead of the human subject E has attached thereto an electrode of the sensor 11, and the sensor 11 detects brain waves ($\alpha$ wave, $\beta$ wave, $\delta$ wave, $\theta$ wave, etc.) of the human subject E. The left wrist of the human subject E has attached thereto the sensor 12, and the sensor 12 detects pressure changes in the radial artery, i.e., a pulse wave, for example. Since a pulse wave is synchronous with a heartbeat, the sensor 12 indirectly detects a heartbeat. Inside a pillow there is provided the sensor 13 for detecting pressure changes and/or acceleration, so that the sensor 13 detects respiration, heartbeat and so on from body motion of the human subject E.

It is of note that the sensor 13 may be provided in different positions other than inside the pillow if, even at a different position, the sensor 13 can still detect the respiration, heartbeat and so on, of the human subject E. For example, the sensor 13 may be positioned between the pillow and the head of the human subject E, on the mattress, the sheet, etc., or inside the bed 5. Alternatively, the respiration, heartbeat, and so on may also be detected indirectly by way of reflected radio waves, sound waves, etc.

Signals detected by the sensors 11, 12 and 13 are supplied to the sleep guidance device 20.

While the drawing illustrates a case where a single sensor 11 is attached to the forehead of the human subject E, multiple ones of the sensor 11 may be attached at different positions. For the sake of convenience, the drawing illustrates a configuration in which the detected signals of the sensors 11, 12 and 13 are transmitted to the sleep guidance device 20 in wired form. Alternatively, wireless transmission may be employed instead. In a case where a heartbeat can be detected by the sensor 11, the sensor 12 may be omitted.

The sleep guidance device 20 serves to estimate sleep depths of the human subject E by processing the detected signals of the sensors 11, 12 and 13. The sleep guidance device 20 also serves to control a sound source such that, in accordance with the biorhythms of the human subject E and the estimated sleep depths, the sound source plays a sound to be heard by the human subject E. The sleep guidance device 20 may be a portable terminal or a personal computer, for example. Functional blocks (described later) are realized by a central processing unit (CPU) (not shown) of the sleep guidance device 20 executing a pre-installed program. In the example illustrated in the drawing, the sleep guidance device 20 is illustrated as a personal computer, but the sleep guidance device 20 may instead be provided inside the pillow, for example.

In this example, the loudspeaker 14 is provided inside the pillow, and causes a sound output from the sleep guidance device 20 to be heard by the human subject E. An alternative configuration may employ headphones, to cause a sound to be heard by the human subject E. However, the present embodiment is explained based on a configuration in which the loudspeaker 14 is used.

Figure 2A:
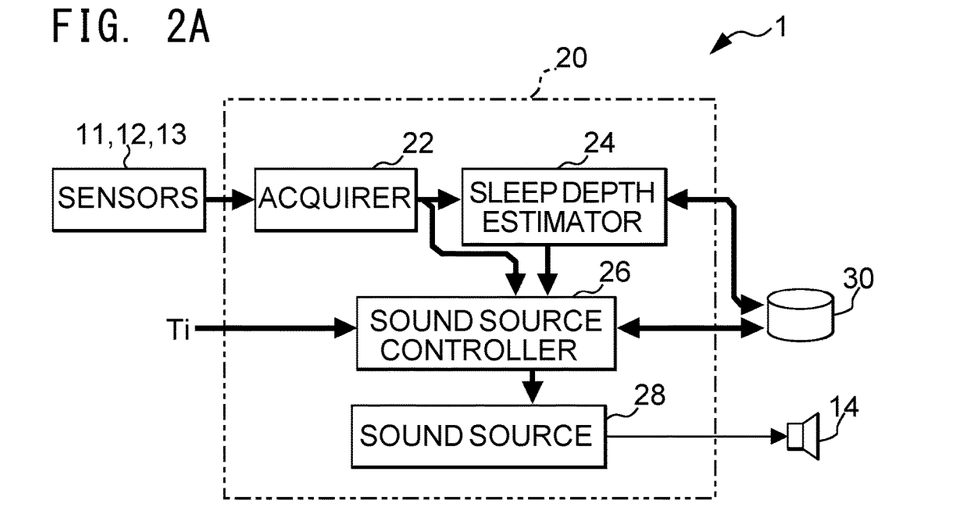
FIG. 2A is a block diagram illustrating a functional configuration of the system.

FIG. 2A mainly illustrates a configuration of functional blocks in the sleep guidance device 20 of the system 1. As illustrated in this drawing, the sleep guidance device 20 includes an acquirer 22, a sleep depth estimator 24, a sound source controller 26, and a sound source 28. These functional blocks are realized by the CPU executing the aforementioned program.

Figure 2B:
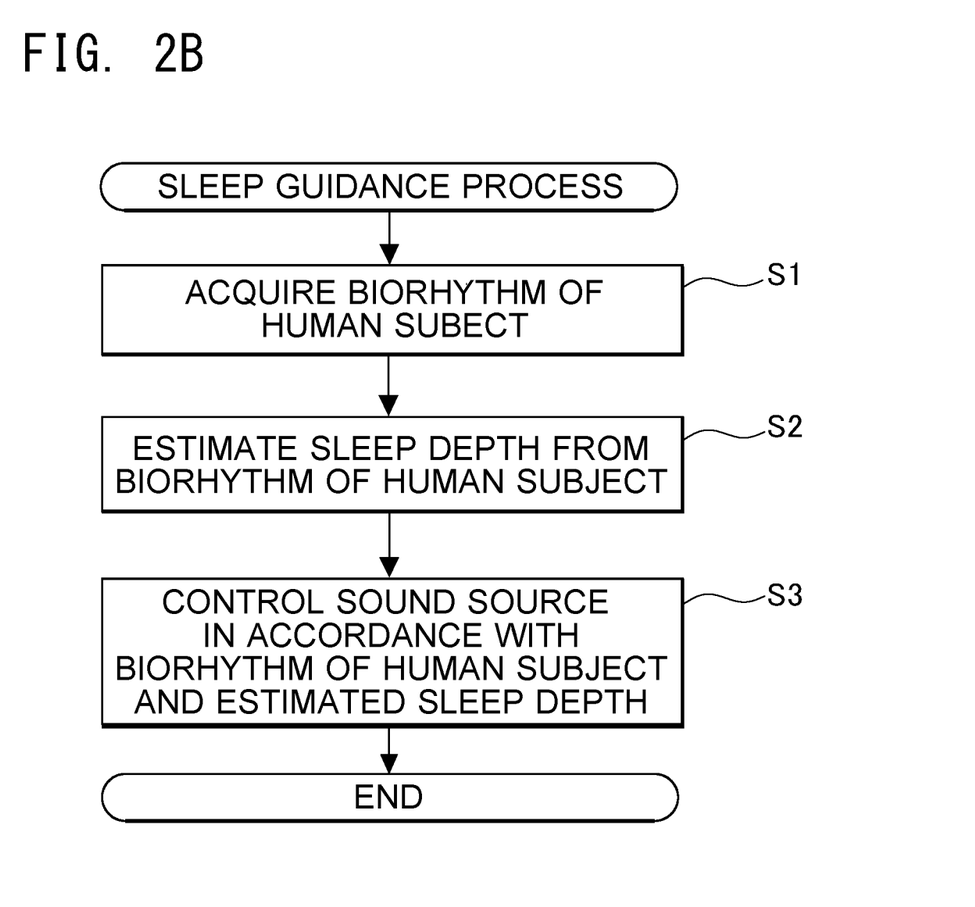
FIG. 2B is a flowchart illustrating a flow of a sleep guidance process.

FIG. 2B is a flowchart illustrating a flow of a sleep guidance process executed by the CPU of the sleep guidance device 20. As illustrated in this drawing, the CPU acquires biorhythms (a brain wave, a pulse wave, respiration, heartbeat, etc.) of the human subject E from the sensors 11, 12 and 13 (S1), and estimates sleep depths of the human subject E from the acquired biorhythms of the human subject E (S2). Next, the CPU controls the sound source 28 to play a sound in accordance with the acquired biorhythms and a current sleep depth among the estimated sleep depths (S3). This control may bring about a change in a sleep depth that is estimated for the human subject E at a subsequent time point.

The acquirer 22 in FIG. 2A converts the detected signals of the sensors 11, 12 and 13 into digital signals and temporarily accumulates the same in an internal memory, then supplies the signals to the sleep depth estimator 24 and the sound source controller 26.

The sleep depth estimator 24 has a memory, and based on detection results of the sensors 11, 12 and 13, estimates whether a current sleep depth of the human subject E corresponds to non-REM sleep, REM sleep, or wakefulness. In estimating sleep depths in the present embodiment, non-REM sleep is divided into four stages 4 to 1 in decreasing order of depth of sleep. A total of six stages are used for estimating sleep depths for the sake of convenience. Alternatively, sleep depths may be estimated without being defined in stages. Characteristics of estimated sleep depths (described later) will be shown in the drawings without being defined in stages.

An approach such as the following may be employed to estimate sleep depths. Specifically, a calm state in which there is relatively little body motion yet a β wave is dominant is defined as "wakefulness", whereas a state in which a θ wave is present yet respiration is shallow and irregular is defined as "REM-sleep". In non-REM sleep, a state of light non-REM sleep where a θ wave is present is defined as "stage 1"; and a state of deep non-REM sleep where a δ wave is present is defined as "stage 4". Between "stage 1" and "stage 4" is sectioned into two stages, which are defined as "stage 2" and "stage 3", in order from "stage 1".

The sound source controller 26 controls the sound source 28 such that the sleep depth estimated for the human subject E is REM-sleep at an awakening time Ti set in advance.

Non-REM sleep and REM sleep generally occur alternately and are repeated at around 90-minute cycles during human sleep, although the length of each cycle may vary from person to person. Further, it is said a person is likely to feel refreshed if the person awakes from REM sleep in one of the cycles.

Accordingly, in the present embodiment, the sleep depth of the human subject E is guided such that the sleep depth is REM-sleep at an awakening time Ti.

It is also said a person is more likely to relax and fall asleep when subjected to stimuli at cycles that are longer than cycles of biorhythms, such as heartbeat, respiration, and brain waves. On the other hand, when subjected to stimuli at shorter cycles than cycles of biorhythms, a person is more likely to become excited and awaken. In the sleep guidance device 20 according to the present embodiment sound is used as an example of stimuli, i.e., an auditory stimulus.

A person is more likely to relax and fall asleep when hearing a sound that has a pitch (pace) or tempo having longer cycles than those of his/her biorhythms. In contrast, a person is more likely to become excited and awaken upon hearing a sound that has a pitch (pace) or tempo having shorter cycles than his/her biorhythms. Moreover, a person is more likely to fall asleep when hearing ultrasound at a frequency of 20 kHz or above.

A person is more likely to awaken when hearing a stimulating sound (a sound that attracts an attention of the human subject), at a loudness of approximately 50 phons in a case where the stimulating sound is an intermittent sound, or at a loudness of approximately 55 phons in a case of a continuous sound. In contrast, a person is more likely to fall asleep when hearing a non-stimulating sound at a loudness of less than 40 phons in a form of a continuous sound. Accordingly, the sleep depth of the human subject E is guided to a target sleep depth by use of, for example, a pitch (pace), tempo, frequency, a loudness or a type of sound, or by a combination of the same.

As described below, the sound source controller 26 controls the sound source 28 such that, in accordance with a current sleep depth of the human subject E estimated by the sleep depth estimator 24, the sound source 28 either lengthens or shortens the cycles of the sound to be heard by the human subject E, relative to the cycles of biorhythms of the human subject E detected by the sensors 12 and 13. In this manner, the sound source controller 26 guides the sleep depth to be REM sleep at the awakening time Ti. The sound source 28 and the loudspeaker 14 together serve as a stimulus imparter that imparts to the human subject E a sound that acts as a stimulus (a stimulus that may affect the sleep depth of the human subject E). In addition, the sound source controller 26 serves as a stimulus controller that controls the stimulus imparter to impart a stimulus to the human subject E in accordance with the biorhythms of the human subject E acquired by the acquirer 22, and a current sleep depth estimated by the sleep depth estimator 24.

The sound source controller 26 causes characteristics that indicate a manner in which sleep depths estimated for the past sleep of the human subject E changed over time, to be recorded in a database 30.

In accordance with the control performed by the sound source controller 26, the sound source 28 generates a digital signal of, for example, white noise. Specifically, in accordance with the control performed by the sound source controller 26, the sound source 28 causes white noise to fade in near a start point of a cycle of a biorhythm (e.g., a cycle of heartbeat) acquired by the acquirer 22, and causes the same to fade out near an end point thereof. Thus, in accordance with the control performed by the sound source controller 26, the sound source 28 generates a signal in which cycles of a periodically-changing element (amplitude, pitch, etc.) of a sound change in accordance with changes in cycles of the biorhythm (i.e., the sound element in this signal is linked with the biorhythm).

Furthermore, in accordance with the control performed by the sound source controller 26, the sound source 28 generates a signal in which the cycles of the sound element linked with the biorhythm are either lengthened or shortened in accordance with a current sleep depth estimated by the sleep depth estimator 24.

The signal thus generated is converted into an analog signal, and the analog signal is then output from the loudspeaker 14 as a sound to be heard by the human subject E.

The sound source 28 may generate not only white noise but also nature sounds (sounds of gentle waves, wind, etc.) having a cyclic nature, or instrumental sounds, such as those of a bell and piano. In this case, by the sound source controller 26 controlling a playback speed (tempo) of waveform data indicative of the nature sounds or instrumental sounds, the sound source 28 is able to play a sound having cycles that are either longer or shorter relative to the cycles of biorhythms in accordance with a current sleep depth estimated by the sleep depth estimator 24.

The database 30 stores waveform data of multiple types of nature sounds and instrumental sounds. Preferably, the cycles of the nature sounds or instrumental sounds (i.e., the cycles of the sound element) in the waveform data may be determined in advance, and in accordance with the control performed by the sound source controller 26, the sound source 28 may control the playback speed of the waveform data such that: the cycles of the waveform data played are linked with the cycles of the heartbeat acquired by the acquirer 22; and at the same time, the cycles of the waveform data played are either longer or shorter in accordance with a current sleep depth estimated by the sleep depth estimator 24. The same is applicable when the biorhythm which the waveform data is to be linked with is respiration or a brain wave.

In place of waveform data of nature sounds or instrumental sounds, the sound source 28 may play a piece of music that is compatible with the biorhythms acquired by the acquirer 22. When one beat cycle in the tempo (BPM) of a piece of music is the same as (or is close to) one cycle of a biorhythm, this piece of music may be understood as a sound having the same tempo as the biorhythm. Accordingly, in accordance with the control performed by the sound source controller 26, the sound source 28 modifies the tempo of the piece of music having the same tempo as the biorhythm, to thereby generate a sound that has either longer or shorter cycles than the biorhythm. When the piece of music is in the form of MIDI-format data, an advantage is obtained in that it is possible to change the tempo simply by indicating a tempo in MIDI. The data of a piece of music may be pre-stored in the database 30, or may be acquired from a separate device by means of communication.

The cycles of a heartbeat resemble a general tempo of music. Meanwhile, a respiration has a longer cycle than a cycle of a heartbeat. Therefore, when a piece of music is linked with respiration cycles, it is preferable that a single cycle of a piece of music be constituted by a given multiple of a beat (4 beats, 5 beats, etc.), instead of a single beat. In this case, a sound is regarded as having the same tempo as a biorhythm when a cycle constituted by a given multiple of a beat is the same as (or is close to) a cycle of the biorhythm.

The sound source 28 in this example has been explained in terms of a so-called software sound source created by executing a computer program, but needless to state, the sound source 28 may be realized in the form of hardware instead.

Figure 3:
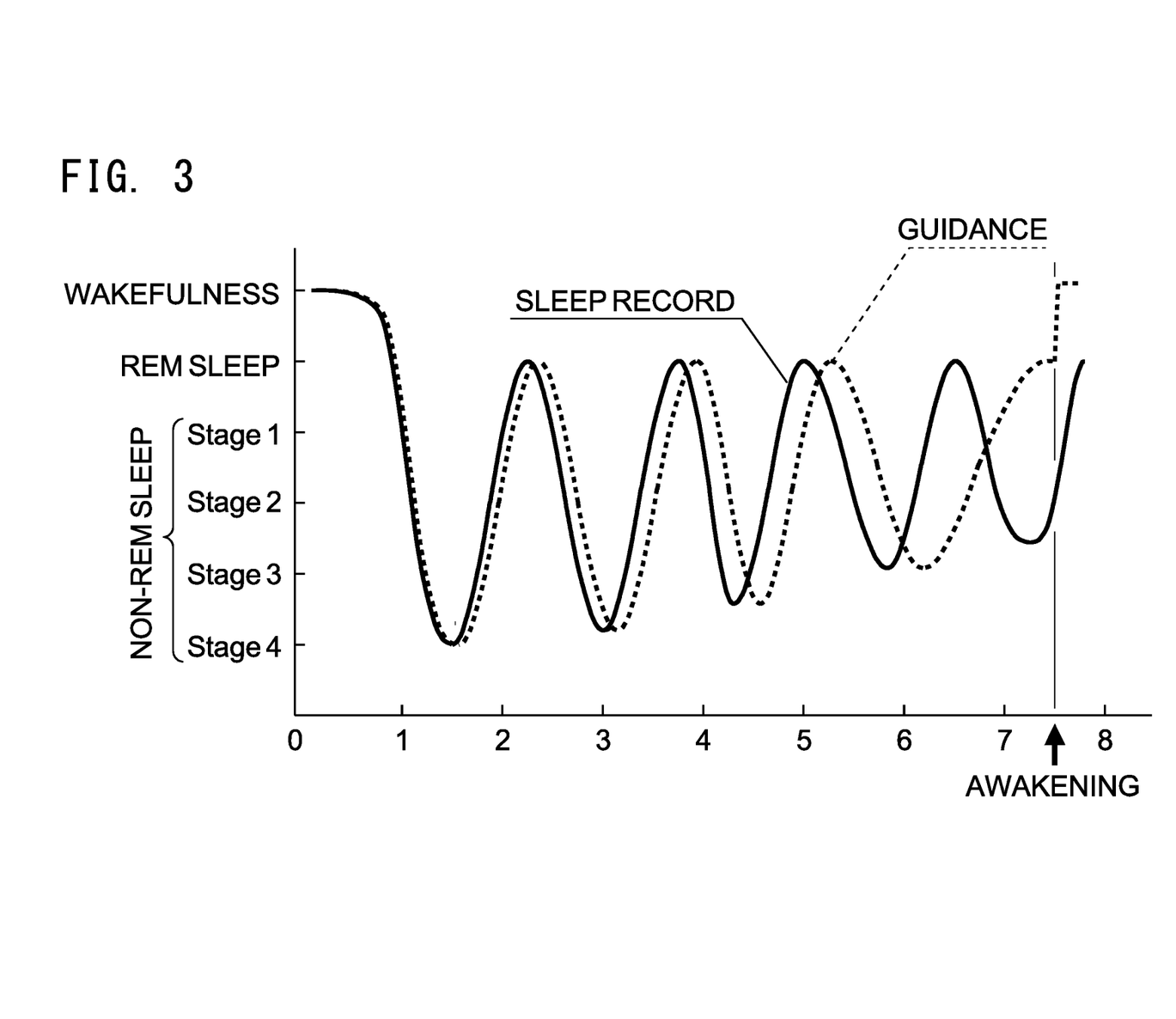
FIG. 3 illustrates characteristics of sleep depths estimated by the sleep guidance device.

FIG. 3 illustrates an example of characteristics of sleep depths of the human subject E estimated by the sleep guidance device 20.

The solid line in this figure indicates an average of multiple sleep depths estimated for the human subject E at prior time points. These sleep depths are sleep depths estimated under natural conditions, i.e., conditions where a sleep depth is not being guided by the sound source controller 26 to a desired sleep depth. Such an average of sleep depths can be obtained by, for example, estimating and recording sleep depths over time for a single sleep period extending from sleep onset to awakening, and averaging the sleep depths that have been estimated and recorded for multiple sleeps.

With regard to sleep depths, as is indicated by the solid line, non-REM sleep and REM sleep generally repeat at around 90-minute cycles. Deepest values of sleep depths tend to show a gradual rise over time (i.e., the sleep depth becomes gradually lighter). A "deepest value" as referred to herein is a value corresponding to a deepest point that a sleep depth reaches in a transitional course of REM sleep→non-REM sleep→REM sleep. It is of note that a deepest value may not only be a local minimum obtained at a point where a fall turns into a rise, but may also be a horizontal value corresponding to a value that remains constant (horizontal) between a fall and a rise.

To cause the sleep depth to be REM-sleep at the awakening time Ti, the sound source controller 26 modifies the characteristics of the averaged sleep depth (solid line), by extending or contracting the characteristics along a time axis (the modified characteristics are indicated by the broken line and will hereinafter be referred to as "target characteristics"). Specifically, the sound source controller 26 first obtains a set sleep period by converting an awakening time Ti set by an input unit (not shown) into a time that passes from the start of the sleep depth estimation. For example, when the time of sleep onset is 11 pm and the set awakening time is 6:30 am the following day, the sound source controller 26 obtains a set sleep period of 7 hours and 30 minutes from the start of the estimation of the sleep depths indicated by the solid line. The sound source controller 26 then modifies the characteristics of the sleep depth indicated by the solid line by either extending or contracting the same, such that it will be REM sleep when the set sleep period expires. In other words, for the purpose of extending along the time axis the characteristics indicative of time changes in the averaged sleep depths, the sound source controller 26 gradually delays phases in the characteristics, whereas for the purpose of contracting the characteristics, the sound source controller 26 gradually advances the phases. In this way, the sound source controller 26 modifies the characteristics such that it will be REM sleep when the set sleep period expires. In the example shown in the figure, the characteristics of the averaged sleep depths are extended along the time axis (i.e., the phases are gradually delayed) such that the time point at which the set sleep period expires falls within the range of REM sleep.

The sound source controller 26 controls the sound source 28 such that the time changes in the sleep depths estimated from the detection results of the sensors 11, 12 and 13 approach the modified characteristics (target characteristics) of the sleep depth.

Specifically, when the estimated sleep depth is deeper than the modified sleep depth in a case where the estimated sleep depths are changing toward a deeper sleep state, the sound source controller 26 controls the sound source 28 to generate a sound having a shorter cycle than the cycle of the biorhythm such that the transition speed of the estimated sleep depths changing toward a deeper sleep state decreases (i.e., so that actual deepening of the sleep depth of the human subject becomes slower). On the contrary, when the estimated sleep depth is lighter than the modified sleep depth in a case where the estimated sleep depths are changing toward a deeper sleep state, the sound source controller 26 controls the sound source 28 to generate a sound having a longer cycle than the cycle of the biorhythm such that the transition speed of the estimated sleep depths changing toward a deeper sleep state increases (i.e., so that actual deepening of the sleep depth of the human subject becomes faster).

When the estimated sleep depth is lighter than the modified sleep depth in a case where the estimated sleep depths are changing toward a lighter sleep state, the sound source controller 26 controls the sound source 28 to generate a sound having a longer cycle than the biorhythm so that the transition speed of the estimated sleep depths changing toward a lighter sleep state decreases. On the contrary, when the estimated sleep depth is deeper than the modified sleep depth in a case where the estimated sleep depths are changing toward a lighter sleep state, the sound source controller 26 controls the sound source 28 to generate a sound having a shorter cycle than the biorhythm so that the transition speed of the estimated sleep depths changing toward a lighter sleep state increases.

As a result of such control, the actual sleep depth of the human subject E changes almost in exact correspondence with the modified characteristics (target characteristics). Accordingly, the sleep depth becomes REM sleep as the set sleep period expires, and the human subject E is able to awaken refreshed and experience improved sleep satisfaction as a result. Thus, the sleep guidance device 20 of the present embodiment controls cycles of a sound (stimulus) imparted to a human subject in accordance with biorhythms of the human subject, and sleep depths estimated by the sleep depth estimator 24 from the biorhythms, and the sleep depth of the human subject E is caused to change accordingly such that sleep satisfaction of the human subject E is improved.

It is of note that the sound source controller 26 may guide the human subject to wakefulness, for example, by increasing a tempo and/or loudness of the sound at the time point at which the set sleep period expires.

In the present embodiment, it is preferable that the sleep depth be guided to a desired state in a manner stated below, so that in addition to sleep satisfaction, sleep quality also is improved.

Figure 4:
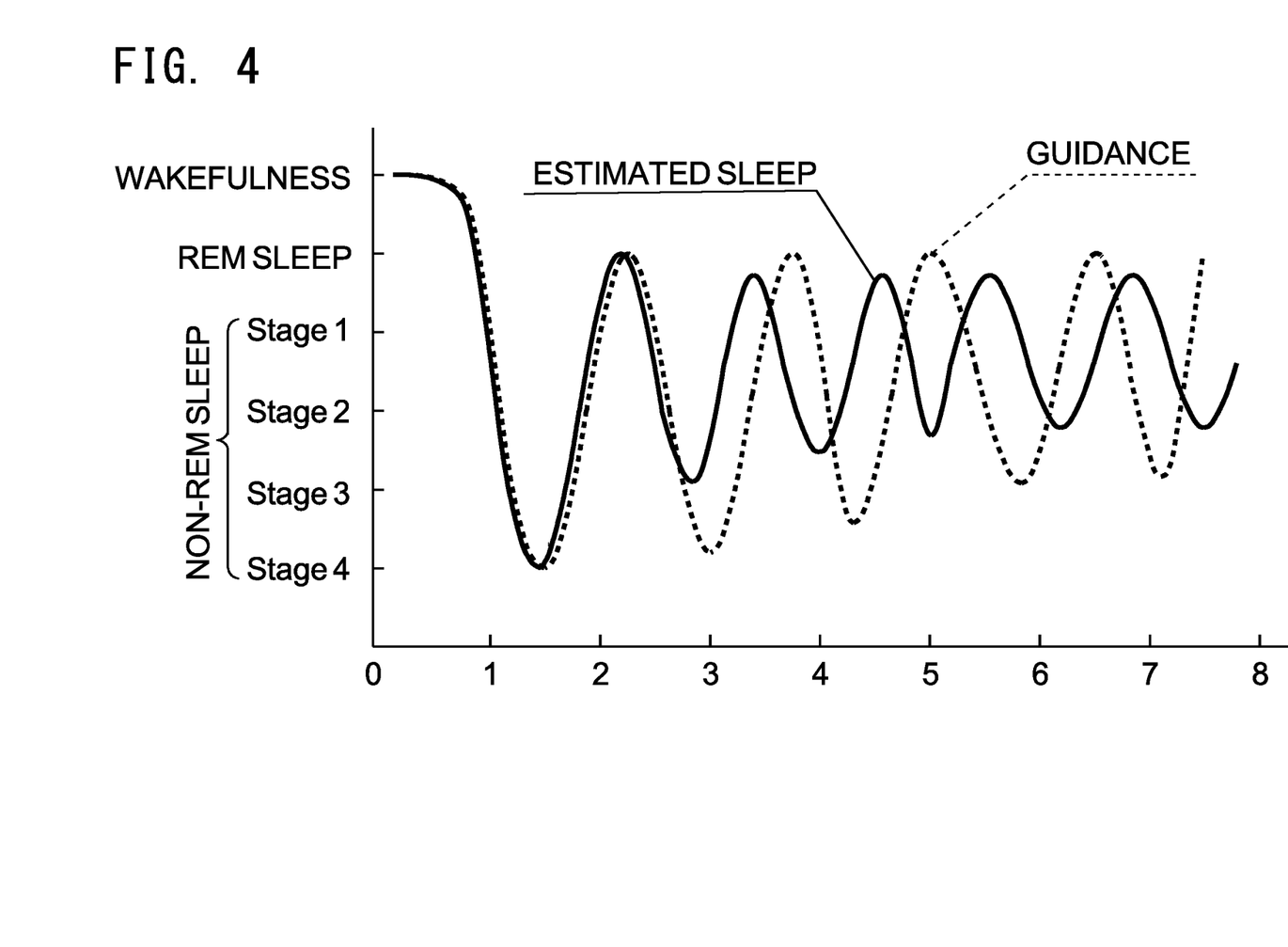
FIG. 4 illustrates characteristics of sleep depths estimated by the sleep guidance device.

FIG. 4 illustrates an example of characteristics of sleep depths in a case where sleep quality of the human subject E is improved by the sleep guidance device 20.

The solid line in the figure indicates an example in which sleeping cycle disorders are observed in the characteristics of the sleep depths of the human subject E estimated under a natural condition where the sleep depth is not being guided to a desired sleep depth. Specifically, an exemplary case is illustrated where cycles (sleeping cycles) at which non-REM sleep and REM sleep are repeated are short and deepest values of the sleep depth in non-REM sleep are small (i.e., sleep is light). As a result of sleeping in such a manner, the human subject E would feel sleep-deprived or awaken in an unsettled mood.

The characteristics of the sleep depths as indicated by the solid line in FIG. 4 may be estimated as follows, for example. Specifically, the characteristics are estimated: from change characteristics of a plurality of the sleep depths of the human subject E that are obtained between sleep onset and a current time point, the sleep depths having been stored in the memory of the sleep depth estimator 24; and from the characteristics of the sleep depths stored in the database 30, which were estimated with regard to a past sleep of the human subject E.

The sound source controller 26 controls the sound source 28 such that the sleep depths estimated by the sleep depth estimator 24 will have sleep depth characteristics (broken line) (target characteristics) of a sleep, with respect to the human subject E, that was evaluated in the past as favorable under a natural condition (where the sleep depth was not guided to a desired sleep depth), in at least one of the following cases. Namely, in the characteristics obtained by the sleep depths of the human subject E estimated from the detection results of the sensors 11, 12 and 13 being sequentially stored in the memory, one of the cases is where respective sleeping cycle lengths are shorter than a threshold (or a degree of irregularity in the sleeping cycle lengths is equal to or more than a prescribed value); and the other case is where sleep is lighter than a threshold (specifically, the respective deepest values of the sleep depth in non-REM sleep are smaller than a threshold). Specific details of the control performed by the sound source controller 26 on the sound source 28 are substantially the same as the details explained with respect to FIG. 3.

Thus, sleep quality can be improved such that sleeping cycles are longer and sleep is deeper.

Regarding characteristics of sleep depths indicated by the broken line (target characteristics), characteristics of sleep that the human subject E evaluated as favorable after awakening may be accumulated in the database 30, and those characteristics may be read for use as the target characteristics.

To improve sleep quality, the sound source controller 26 may control the sound source 28 to output the aforementioned ultrasound, thereby guiding the human subject E toward relaxation (a direction in which a depth of sleep increases).

Moreover, sounds having positive effects or negative effects, for instance, on sleep may be estimated from past records and applied appropriately to improve sleep quality. Alternatively, light, fragrance, temperature, humidity, vibration, or other stimuli that may affect a depth of sleep of the human subject E may be used to guide the sleep depth to a depth that is desired.

In the present embodiment, by accelerating a transition from REM sleep to non-REM sleep in the following manner, a sleep period can be reduced while ensuring sleep quality.

Figure 5:
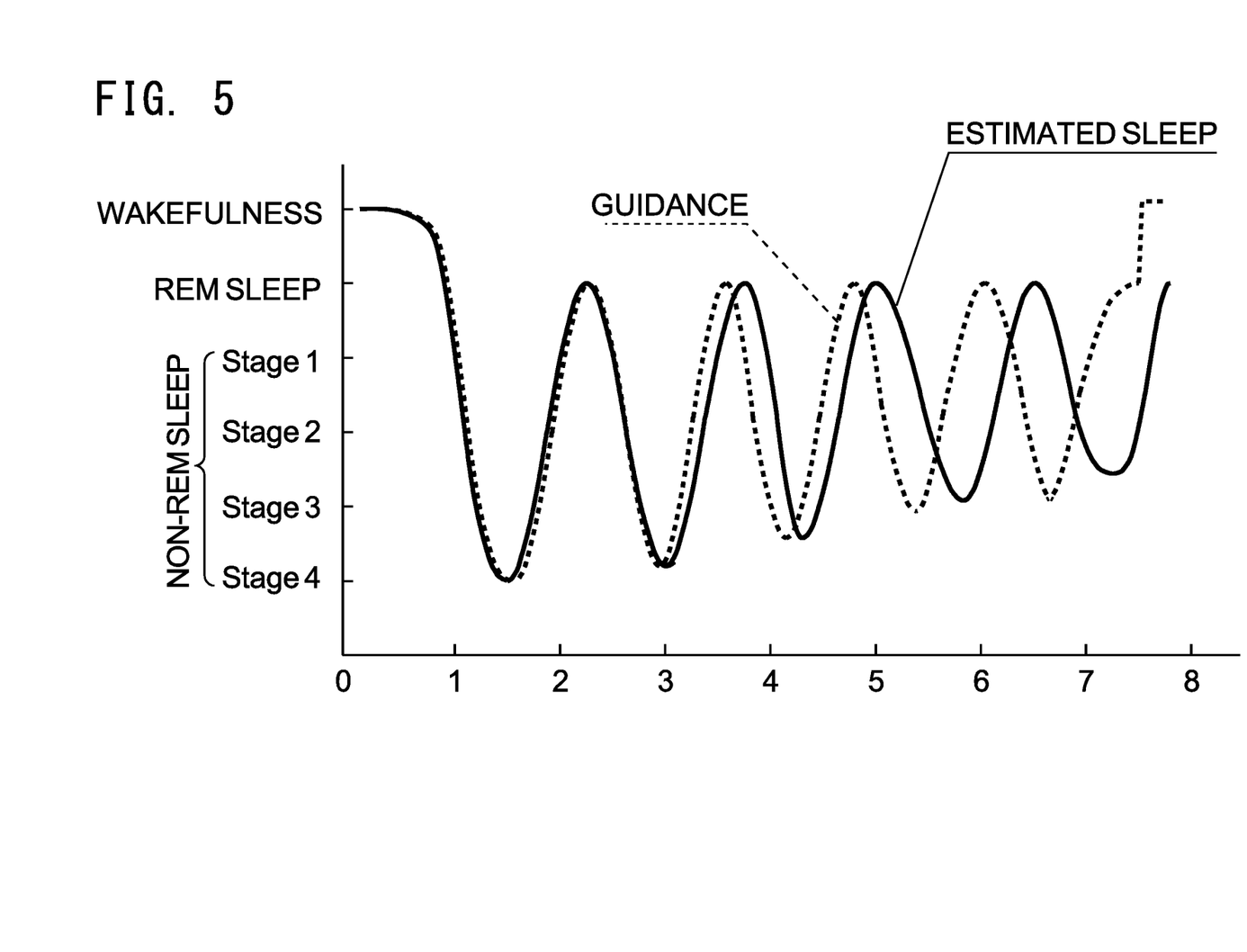
FIG. 5 illustrates characteristics of sleep depths estimated by the sleep guidance device.

FIG. 5 illustrates an example of characteristics of sleep depths in a case where a sleep period of the human subject E is reduced by the sleep guidance device 20.

The solid line in this figure indicates characteristics of sleep depths that are estimated under a natural condition where the sleep depth is not being guided to a desired sleep depth.

The sound source controller 26 modifies the characteristics such that a transition from REM sleep to non-REM sleep in the characteristics is accelerated, and the modified characteristics such as those indicated by the broken line are set as target characteristics. In this modification, a transition to REM sleep is accelerated on condition that a duration of immediately preceding non-REM sleep is equal to or greater than a threshold. The reason for providing such a condition is that simply accelerating a transition from non-REM sleep to REM sleep would result in a failure to ensure a sufficient sleeping time in non-REM sleep, which would compromise sleep quality.

The sound source controller 26 controls the sound source 28 such that the time changes in the sleep depths estimated from the detection results of the sensors 11, 12 and 13 will have the target characteristics (broken line). Specific details of the control performed by the sound source controller 26 on the sound source 28 are substantially the same as those described with respect to FIG. 3.

According to the above, improvements are achieved in terms of the lengths of the sleeping cycles being shortened and sleep being deepened.

The characteristics of the sleep depths as indicated by the solid line in FIG. 5 are estimated: from change characteristics of a plurality of sleep depths of the human subject E that are obtained between sleep onset and a current time point, the sleep depths being stored in the memory of the sleep depth estimator 24; and from the characteristics of the sleep depths stored in the database 30, which were estimated with regard to a past sleep of the human subject E.

In the present embodiment, a person for whom a sleep depth is guided has been one individual only. However, a number of people may be two as described below, or three or more.

Figure 6:
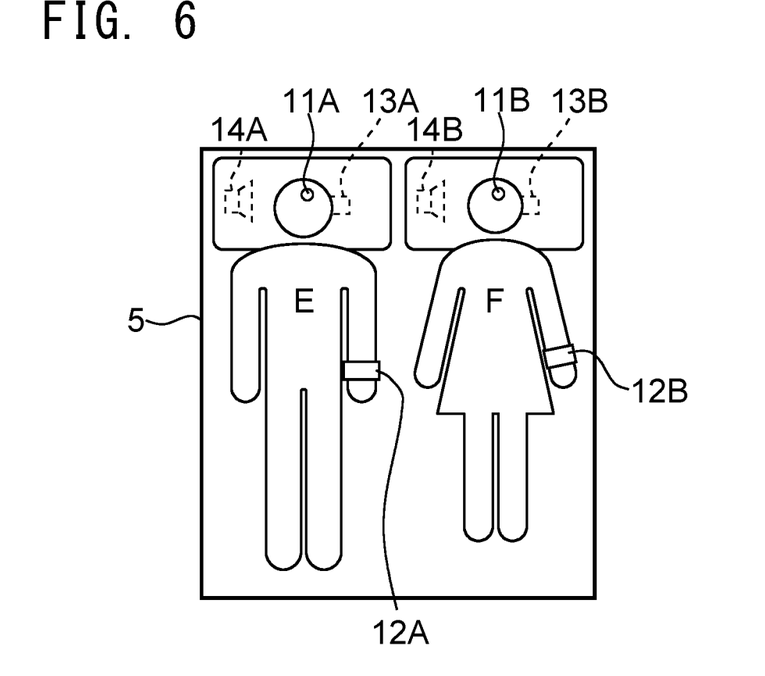
FIG. 6 illustrates an arrangement of sensors, etc., according to an application example of the sleep guidance device.

FIG. 6 illustrates an arrangement of sensors, etc., in a case where the sleep guidance device 20 guides sleep depths of two human subjects E and F to desired sleep depths, the two human subjects E and F being partners.

As illustrated in this drawing, the human subjects E and F are lying on their backs on the bed 5. Sensors 11A, 12A and 13A detect biorhythms of the human subject E, whereas sensors 11B, 12B and 13B detect biorhythms of the human subject F. Here, the sleep guidance device 20 is configured to include two sound sources 28 and two sound source controllers 26 each controlling a corresponding one of the two sound sources 28 independently in accordance with detected signals from the human subjects E and F. That is to say, the sleep guidance device 20 includes two sets of the configuration illustrated in FIG. 2A, and causes the human subject E to hear a sound by means of a loudspeaker 14A and causes the human subject F to hear a sound by means of a loudspeaker 14B. A configuration may also be adopted in which a part of the configuration illustrated in FIG. 2A is shared by the loudspeakers 14A and 14B. Even in this configuration, control can be performed independently for each of the human subjects E and F, as in the method described above.

Meanwhile, when guidance to a desired sleep depth is not performed on the human subject E, the sound source controller 26, the sound source 28, and the loudspeaker 14A, which are associated with the human subject E, may be omitted.

In a case where two human subjects are sleeping on the same bed 5 as in the present case, it is conceivable that the sleep depth of one (first) human subject may have an impact on the sleep depth of the other (second) human subject. In this respect, an improvement will be considered below for diminishing such an impact.

This impact may be, for example, the sleep of the second human subject being disturbed by snoring of the first human subject during sleep. Snoring occurs during non-REM sleep. The second human subject is liable to notice snoring when his/her sleep is light, i.e., during REM sleep.

Accordingly, in a case where the sleep depth of the second human subject changes in substantially the same manner as the sleep depth estimated for the first human subject, the sleep depth of the second human subject is non-REM sleep (deep sleep) when snoring of the first human subject occurs, so the second human subject is less liable to perceive the snoring.

Figure 7:
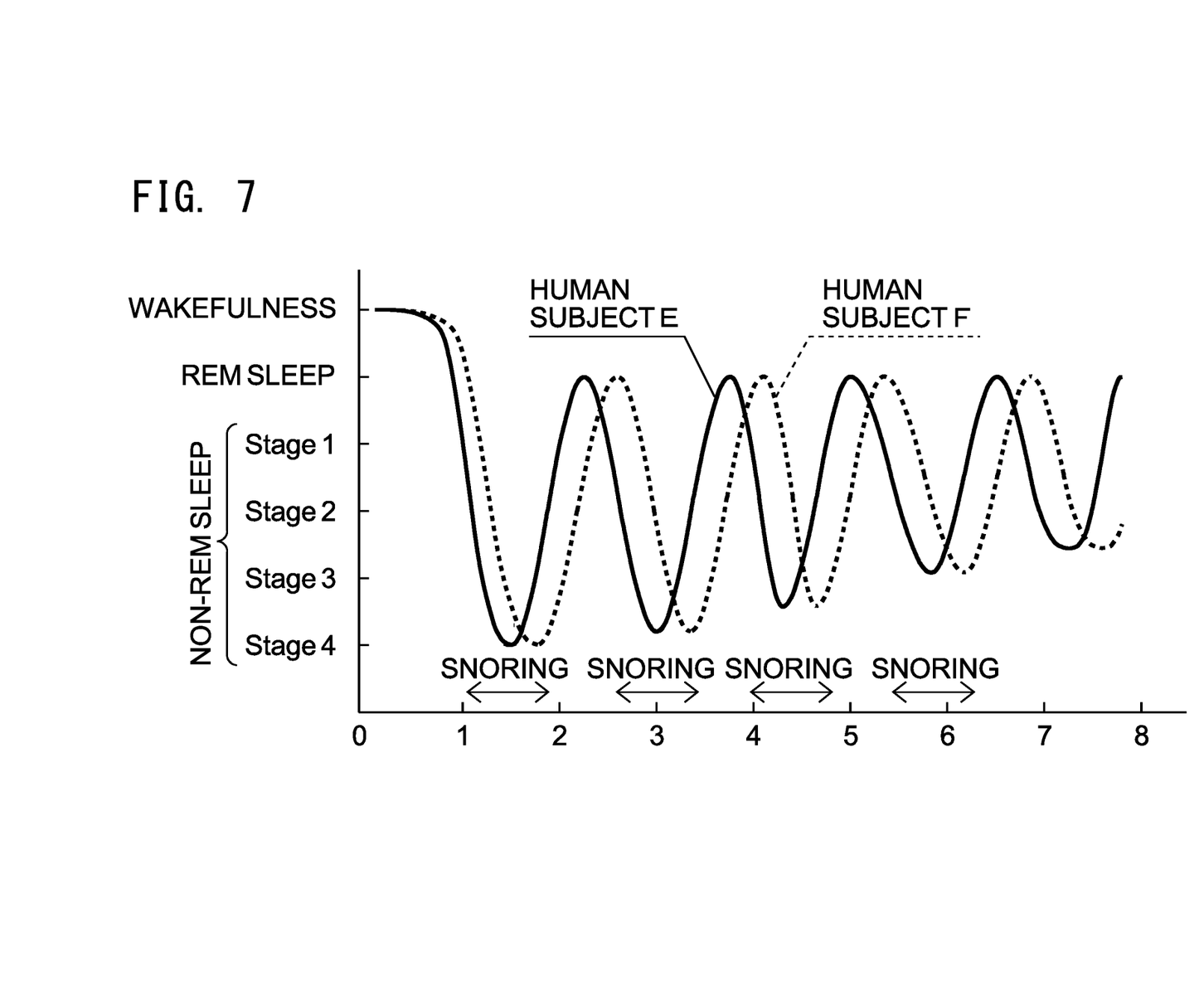
FIG. 7 illustrates characteristics of sleep depths estimated by the sleep guidance device.

FIG. 7 illustrates time changes in sleep depths estimated by the sleep depth estimator 24 for the human subjects E and F. The solid line in this drawing indicates characteristics of sleep depths that are estimated for the human subject E under a natural condition where the sleep depth is not being guided to a desired sleep depth. The sound source controller 26 controls the sound source 28 associated with the human subject F such that the sleep depths of the human subject F will have the characteristics of the sleep depths estimated for the human subject E, i.e., so that phases of the sleep depths of the human subject F are equivalent to phases of the sleep depths of the human subject E.

As a result of such control, the sleep depths (a time waveform thereof) for the human subject F indicated by the broken line change so as to approach the sleep depths (a time waveform thereof) for the human subject E indicated by the solid line. Accordingly, the sleep depth of the second human subject F is non-REM sleep when snoring of the first human subject E occurs, and thus the human subject F is less liable to perceive the snoring, and as a result a negative impact, i.e., disturbance of sleep due to snoring can be minimized.

The characteristics of the sleep depths of the human subject E as indicated by the solid line in FIG. 7 are estimated: from change characteristics of a plurality of sleep depths that are obtained between sleep onset and a current time point, the sleep depths being stored in the memory of the sleep depth estimator 24; and from the characteristics of the sleep depths stored in the database 30, which were estimated with regard to a past sleep of the human subject E.

Further, in a case where sleep of the second human subject is disturbed by sleep talking of the first human subject during sleep for example, the sound source controller 26 controls the sound source 28 associated with the second human subject such that the phases of the characteristics of the sleep depths of the second human subject are reversed relative to the phases of the characteristics of the sleep depths of the first human subject.

The reason for this is that sleep talking occurs during REM sleep (light sleep) in contrast to snoring, and in a case where sleep of the second human subject is deep at a time that sleep talking of the first human subject occurs, the second human subject is less liable to perceive the sleep talking.

In this configuration, the sleep depth of the human subject E may be guided to a desired sleep depth first, and then the sleep depth of the human subject F may be guided such that the phases of the time waveform of the sleep depths of the human subject F are equivalent to, or reversed relative to the phases of the time waveform of the sleep depths of the human subject E.

In the above embodiment, the sensors 11, 12 and 13 (or 11A, 12A and 13A) detect biorhythms of the human subject E, the sleep depth estimator 24 estimates sleep depths, and the sound source controller 26 controls the sound source 28 to generate a sound in accordance with the detected biorhythms and the estimated sleep depths. However, a configuration such as the following may also be adopted.

For example, prior to actual guidance to a desired sleep depth, a brain wave, a pulse wave, respiration, etc., of the human subject E during sleep is detected to estimate sleep depths, and a simple sensor (e.g., an acceleration sensor serving to detect body motion) is additionally employed for the detection at the same time. The estimated sleep depths and detection results of the simple sensor are associated with each other and stored in a memory (e.g., the memory of the sleep depth estimator 24). Then, in actual guidance to a desired sleep depth, the simple sensor alone is attached to the human subject E in place of the sensors 11, 12 and 13 (or 11A, 12A and 13A); based on a detection result obtained by detection by the simple sensor, the sleep depth estimator 24 estimates a sleep depth from correspondences with the sleep depths stored in the memory; and the sound source controller 26 controls the sound source 28 in accordance with the estimated sleep depths. In this case, to associate sleep depths with detection results of a simple sensor, detection results obtained by averaging detection results from a large number of human subjects may be used instead of detection results of only the human subject E.

The estimated sleep depths may also be associated with a playback sound and thus be recorded. When the playback sound is recorded in this way, data accumulated in the database 30 may be statistically analyzed, and categorized into sounds that have achieved guidance to a desired sleep depth and sounds that have failed to do so. In this way, a sound to be used in subsequent guidance may be selected accordingly.

In the above embodiment, a sound is given as an example of stimuli, but stimuli that appeal to other sensory organs may also be used. For example, fragrance (olfactory stimulus), or ambient light (visual stimulus), or temperature, humidity, or vibration (tactile stimulus), or other relevant stimuli may be used alone, or two or more of the above stimuli including sound may be used in appropriate combination, so as to guide a sleep depth to a desired sleep depth.

An example will now be explained in which vibration is used as a stimulus.

Figure 8:
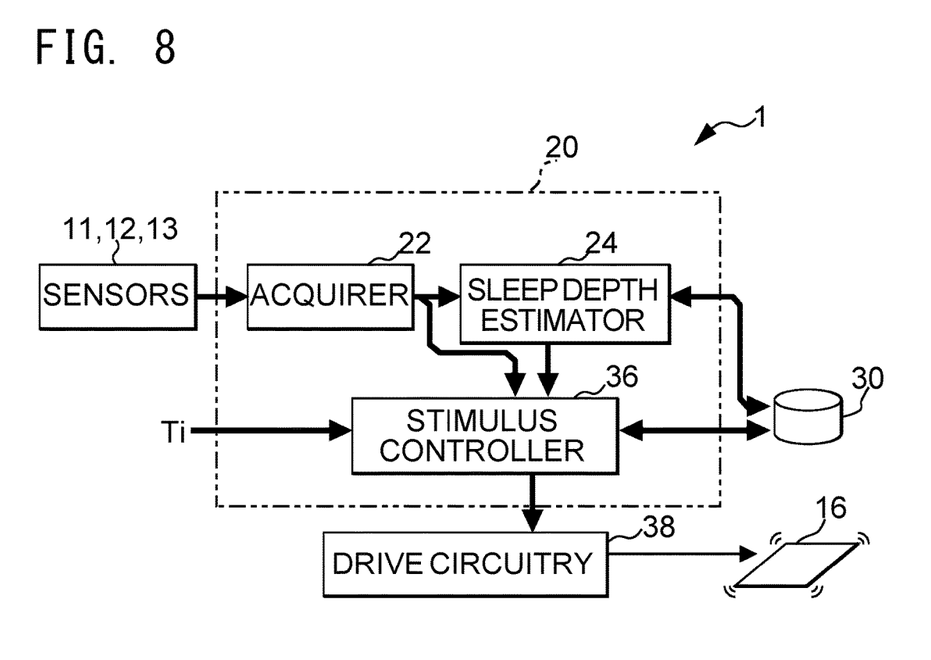
FIG. 8 illustrates a functional configuration of a system according to an application example.

FIG. 8 illustrates a functional configuration of a system according to an application example. Here, a case is assumed where vibration is employed as a specific example of a stimulus. In FIG. 8, the sound source controller 26, the sound source 28, and the loudspeaker 14 in FIG. 2A are replaced with a stimulus controller 36, drive circuitry 38, and an actuator 16, respectively.

Among these, the actuator 16 is, for example, a piezoelectric element that vibrates at a tempo (cycle) and magnitude (amplitude) that are in accordance with a drive signal, and the actuator 16 is provided inside a pillow or the like. The stimulus controller 36 controls the drive circuitry 38 such that the tempo, magnitude, etc., of the vibration that the actuator 16 imparts to the human subject E are in accordance with biorhythms detected by the sensors 11, 12 and 13, and with sleep depths estimated from the detected biorhythms. In accordance with the control performed by the stimulus controller 36, the drive circuitry 38 supplies drive signals to the actuator 16. As illustrated in the drawing, the drive circuitry 38 is a hardware element that is provided exterior to the sleep guidance device 20.

In this configuration, the drive circuitry 38 and the actuator 16 serve together as a stimulus imparter, and the stimulus controller 36 controls the actuator 16 by means of the drive circuitry 38 as follows. In guiding sleep toward a deeper sleep state, the stimulus controller 36 controls the actuator 16 by means of the drive circuitry 38 such that the actuator 16 imparts to the human subject E at least one of a vibration having a slower tempo than a biorhythm, and a vibration having 1/f fluctuation (vibration having 1/f fluctuation in tempo (cycle) and/or magnitude (amplitude)). On the other hand, in guiding sleep toward a lighter sleep state, the stimulus controller 36 controls the actuator 16 such that the actuator 16 imparts to the human subject E at least one of a vibration having a faster tempo than a biorhythm, and a vibration having a greater amplitude than the vibration adopted in guiding sleep toward a deeper sleep state.

In a case where temperature and humidity are used as stimuli, a configuration is adopted in which the actuator controlled by the stimulus controller 36 is an air conditioner (AC) provided in a bedroom in which the human subject E sleeps (this configuration is not illustrated in the drawings).

Specifically, the stimulus controller 36 controls the AC such that a room temperature at bedtime is between 16 and 19 degrees Celsius in winter and approximately 26 degrees Celsius in summer. Under these room temperatures, a neutral temperature would be about 29 degrees Celsius assuming that a thin towel or sheet is used as a cover in summer, and a heavy blanket or the like is used as a cover in winter. The term "neutral temperature" is used here to mean an ambient temperature at which normal body temperature of an unclothed person is maintained. In guiding sleep toward a deeper sleep state after sleep onset, the stimulus controller 36 controls the AC such that the room temperature drops by a few degrees and the humidity is maintained at between 50% and 60%. On the other hand, in guiding sleep toward a lighter sleep state, the stimulus controller 36 controls the AC such that both temperature and humidity rise.

When ambient light is used as a stimulus, lighting may be arranged proximate to the human subject E. A color and luminance of the lighting can be varied, and controlled as follows. In guiding sleep toward a deeper sleep state, the stimulus controller 36 performs control such that illumination is of a cool color and a luminance thereof is approximately 0.3 to 10 lux. Illumination before bedtime may be of a warm color, after which the warm color may be gradually changed to a cooler color from sleep onset onward. On the other hand, in guiding sleep toward a lighter sleep state, the stimulus controller 36 performs control such that the illumination is brightened and has a luminance of approximately 30 to 50 lux. At awakening, however, a luminance may be set to 2,000 lux or higher, or lighting may be caused to flash on and off, on an as-needed basis.

When fragrance is used as a stimulus, an injector that jets a variety of fragrance particles may be arranged proximate to the human subject E, and the injector may be controlled as follows. In guiding sleep toward a deeper sleep state, the stimulus controller 36 controls the injector to jet fragrance with a calming effect, e.g., lavender aroma, cedrol, heliotropine, chamomile aroma, etc. Meanwhile, in guiding sleep toward a lighter sleep state, the stimulus controller 36 controls the injector to jet a fragrance that has an awakening effect, e.g., aromas of peppermint, *eucalyptus*, rosemary, lemon, etc.

A program pertaining to the aforementioned modes may be provided by being stored in a computer-readable recording medium for installation in a computer. For instance, the storage medium may be a non-transitory storage medium, a favorable example of which is an optical storage medium, such as a CD-ROM (optical disc), and may also be a freely-selected form of well-known storage media, such as a semiconductor storage medium and a magnetic storage medium. The programs of the present invention may be provided by being distributed via a communication network for installation in a computer.

The following aspects of the present invention may be derived from the different embodiments and modifications described in the foregoing.

The sleep guidance device according to the aforementioned aspect can change the sleep depth of the human subject by use of a stimulus in accordance with the biorhythm of the human subject and also a current sleep depth, so as to improve sleep satisfaction. A "stimulus" as referred to herein is used to change a depth of sleep of a human subject.

The sleep guidance device according to the aforementioned aspect may be configured in such way in which the stimulus controller controls the stimulus imparter so that, from among the sleep depths, a sleep depth estimated by the sleep depth estimator for the human subject at a time point (e.g., an awakening time) set in advance is light. Thus, in this configuration, the sleep depth of the human subject is guided so as to become lighter toward a set time point, and the human subject awakens, feeling relatively refreshed at the set time point. In this way, an improvement in sleep satisfaction is realized.

The sleep guidance device according to the aforementioned aspect may be configured such that in accordance with a length of a set sleep period, the stimulus controller modifies characteristics indicative of time changes in prior sleep depths of the human subject, and the stimulus controller controls the stimulus imparter such that time changes in the sleep depths estimated by the sleep depth estimator approach the modified characteristics. According to this configuration, the sleep depth of the human subject is guided so as to approach the modified characteristics of sleep depths. Preferably, by either extending or contracting along a time axis the characteristics (sleep waveform) indicative of the time changes in prior sleep depths of the human subject, the stimulus controller modifies the characteristics such that from among the sleep depths, a sleep depth at a time point at which the set sleeping period expires is light. Preferably, the stimulus controller controls the stimulus imparter to impart the stimulus in either shorter or longer cycles than the cycles of the biorhythm of the human subject acquired by the acquirer.

The sleep guidance device according to the aforementioned aspect may have a configuration in which the stimulus controller controls the stimulus imparter such that time changes in the sleep depths estimated by the sleep depth estimator for the human subject remain in a stable deep sleep state.

In the aforementioned aspect, the stimulus controller may be configured so as to control the stimulus imparter such that local minimums of the estimated sleep depths are smaller.

The sleep guidance device according to the aforementioned aspect may have a configuration in which the acquirer further acquires a biorhythm of another human subject differing from the human subject, and the sleep depth estimator estimates the sleep depths of the human subject from the biorhythm of the human subject acquired by the acquirer, and estimates sleep depths of the other human subject from a biorhythm of the other human subject acquired by the acquirer, and the stimulus controller controls the stimulus imparter such that time changes in the sleep depths estimated for the human subject and time changes in the sleep depths estimated for the other human subject have either mutually equivalent phases or mutually reversed phases.

Snoring may occur, for instance, when a sleep depth is deep. For this reason, by controlling a sound source such that time changes in sleep depths of two human subjects have equivalent phases, one of the human subjects is unlikely to be aware of the snoring because s/he is sleeping deeply even if the other human subject is snoring.

Sleep talking may occur, for instance, when a sleep depth is light. For this reason, by controlling a sound source such that time changes in sleep depths of two human subjects have reversed phases, one of the human subjects is unlikely to be aware of the sleep talking because s/he is sleeping deeply even if the other human subject is sleep talking.

It is of note that the present invention may be embodied not only in a form of a sleep guidance device, but also in a form of an operation method that uses a sleep guidance device according to any of different configurations set forth above (i.e., a method of controlling a stimulus imparter for imparting a stimulus to a human subject); or in a form of a program that causes a computer to function as the sleep guidance device; or in a form of a computer-readable recording medium having stored the program thereon. According to the sleep guidance method, program, or computer-readable recording medium having stored the program thereon, each having employed one or more of the aforementioned configurations, substantially the same effects can be attained as those attained by the sleep guidance device as set forth with respect to each of the aforementioned different configurations.

DESCRIPTION OF REFERENCE SIGNS 11, 12, 13: sensor
14: loudspeaker
16: actuator
20: sleep guidance device
24: sleep depth estimator
26: sound source controller
28: sound source
36: stimulus controller

The invention claimed is:

1. A sleep guidance device for controlling a stimulus imparter for imparting a stimulus on a human subject, the device comprising:
    an acquirer configured to acquire a biorhythm of the human subject;
    a sleep depth estimator configured to estimate sleep depths of the human subject from the biorhythm of the human subject acquired by the acquirer; and
    a stimulus controller configured to control the stimulus imparter to impart a stimulus to the human subject in accordance with the biorhythm of the human subject acquired by the acquirer, and from among the sleep depths, a current sleep depth estimated by the sleep depth estimator for the human subject, wherein
    the stimulus controller controls the stimulus imparter to impart the stimulus in either shorter or longer cycles than cycles of the biorhythm of the human subject acquired by the acquirer.

2. The sleep guidance device according to claim 1, wherein
    the stimulus controller controls the stimulus imparter such that, from among the sleep depths, a sleep depth estimated by the sleep depth estimator for the human subject at a time point set in advance is light.

3. The sleep guidance device according to claim 1, wherein
    in accordance with a length of a set sleep period, the stimulus controller modifies characteristics indicative of time changes in prior sleep depths of the human subject, and
    the stimulus controller controls the stimulus imparter such that time changes in the sleep depths estimated by the sleep depth estimator approach the modified characteristics.

4. The sleep guidance device according to claim 3, wherein by either extending or contracting, along a time axis, the characteristics indicative of the time changes in the prior sleep depths of the human subject, the stimulus controller modifies the characteristics such that from among the sleep depths, a sleep depth at a time point at which the set sleeping period expires is light.

5. The sleep guidance device according to claim 1, wherein the acquirer further acquires a biorhythm of another human subject differing from the human subject, the sleep depth estimator estimates the sleep depths of the human subject from the biorhythm of the human subject acquired by the acquirer, and estimates sleep depths of the other human subject from the biorhythm of the other human subject acquired by the acquirer, and the stimulus controller controls the stimulus imparter such that time changes in the sleep depths estimated for the human subject and time changes in the sleep depths estimated for the other human subject have either mutually equivalent phases or mutually reversed phases.

6. A sleep guidance device for controlling a stimulus imparter for imparting a stimulus on a human subject, the device comprising:

an acquirer configured to acquire a biorhythm of the human subject;

a sleep depth estimator configured to estimate sleep depths of the human subject from the biorhythm of the human subject acquired by the acquirer; and a stimulus controller configured to control the stimulus imparter to impart a stimulus to the human subject in accordance with the biorhythm of the human subject acquired by the acquirer, and from among the sleep depths, a current sleep depth estimated by the sleep depth estimator for the human subject, wherein the stimulus controller controls the stimulus imparter such that time changes in the sleep depths estimated by the sleep depth estimator for the human subject remain in a stable deep sleep state.

7. A method of controlling a stimulus imparter for imparting a stimulus to a human subject, the method comprising:

acquiring a biorhythm of the human subject;

estimating sleep depths of the human subject from the acquired biorhythm of the human subject; and controlling the stimulus imparter to impart to the human subject a stimulus having cycles shortened or lengthened relative to cycles of the acquired biorhythm of the human subject in accordance with a current sleep depth, from among the sleep depths, that is estimated for the human subject.

8. A method of controlling a stimulus imparter for imparting a stimulus to a human subject, the method comprising:

acquiring a biorhythm of the human subject;

estimating sleep depths of the human subject from the acquired biorhythm of the human subject; and controlling the stimulus imparter to impart a stimulus to the human subject in accordance with the acquired biorhythm of the human subject, and from among the sleep depths, a current sleep depth estimated for the human subject, such that time changes in the sleep depths estimated for the human subject remain in a stable deep sleep state.

* * * * *